(12) United States Patent
Kolobow

(10) Patent No.: US 7,107,991 B2
(45) Date of Patent: Sep. 19, 2006

(54) ENDOTRACHEAL TUBE USING LEAK HOLE TO LOWER DEAD SPACE

(75) Inventor: Theodor Kolobow, Rockville, MD (US)

(73) Assignee: The United States of America as represented by the Department of Health & Human Services, Washington, DC (US)

( * ) Notice: Subject to any disclaimer, the term of this patent is extended or adjusted under 35 U.S.C. 154(b) by 271 days.

(21) Appl. No.: 09/967,903

(22) Filed: Sep. 28, 2001

(65) Prior Publication Data

US 2003/0062049 A1 Apr. 3, 2003

(51) Int. Cl.
*A61M 16/00* (2006.01)
*A62B 9/06* (2006.01)

(52) U.S. Cl. .............................. 128/207.14; 128/206.29

(58) Field of Classification Search ........... 128/207.14, 128/207.15, 207.16, 206.29, 206.12, 200.26; 604/23

See application file for complete search history.

(56) References Cited

U.S. PATENT DOCUMENTS

| | | | | |
|---|---|---|---|---|
| 3,683,908 | A | * | 8/1972 | Michael et al. ........ 128/207.15 |
| 3,754,554 | A | | 8/1973 | Felbarg |
| 3,880,168 | A | | 4/1975 | Berman |
| 4,155,365 | A | * | 5/1979 | Boslau ................ 128/207.15 |
| 4,334,534 | A | * | 6/1982 | Ozaki ................ 128/207.15 |
| 4,446,864 | A | | 5/1984 | Watson et al. |
| 4,497,318 | A | * | 2/1985 | Donmichael ........... 128/202.28 |
| 4,502,482 | A | | 3/1985 | DeLuccia et al. |
| 4,688,568 | A | * | 8/1987 | Frass et al. ............ 128/207.15 |
| 4,726,373 | A | | 2/1988 | Greengrass |
| 4,892,095 | A | | 1/1990 | Nakhgevany |
| 5,040,532 | A | | 8/1991 | Alfery |
| 5,305,740 | A | | 4/1994 | Kolobow |
| 5,429,127 | A | | 7/1995 | Kolobow |
| 5,501,215 | A | | 3/1996 | Huerta |
| 5,546,936 | A | | 8/1996 | Virag et al. |
| 5,687,714 | A | | 11/1997 | Kolobow et al. |
| 5,766,202 | A | | 6/1998 | Jones et al. |
| 5,906,204 | A | * | 5/1999 | Beran et al. ........... 128/207.14 |

(Continued)

FOREIGN PATENT DOCUMENTS

DE          24 26 344           4/1975

(Continued)

*Primary Examiner*—Michael J. Hayes
*Assistant Examiner*—Michael Mendoza
(74) *Attorney, Agent, or Firm*—Townsend and Townsend and Crew LLP; Guy W. Chambers

(57) ABSTRACT

A tracheal tube ventilation apparatus to more effectively remove expired gases. In one preferred embodiment, one or more leak holes are created in the side walls of an endotracheal tube so that expired gases can leak out of the endotracheal tube above the larynx, such as into the back of the mouth (i.e., oropharynx). Each leak hole might advantageously have a diameter between 0.5 and 4.0 mm. In another preferred embodiment, a tube is attached to a proportionately larger leak hole (e.g., up to 8.0 mm) so that the expired gases can be directed away from the leak hole to a specific location, such as directed out of the mouth. In the case of mechanically controlled ventilation, a positive end expiratory pressure can be applied to this tube to mechanically assist with the process of exhaling. In each of these embodiments, it is preferred, but not required, that the endotracheal tube be an ultra-thin walled, two stage tube so as to further assist in the reduction of resistance to the flow of oxygen/air.

10 Claims, 3 Drawing Sheets

U.S. PATENT DOCUMENTS 5,937,861 A * 8/1999 Augustine ............. 128/207.15
6,055,984 A    5/2000 Brain
6,254,591 B1 * 7/2001 Roberson ................ 604/541

FOREIGN PATENT DOCUMENTS

GB          933307         1/1960

* cited by examiner

ENDOTRACHEAL TUBE USING LEAK HOLE TO LOWER DEAD SPACE

TECHNICAL FIELD OF THE INVENTION

The present invention relates to medical devices to assist patient breathing. More particularly, a tracheal tube ventilation apparatus is disclosed which, through use of one or more endotracheal tube leak holes, or connecting tubes, is able to more efficiently rid the patient of expired gases and thereby promote healthier breathing.

BACKGROUND OF THE INVENTION

Through injury or diseases, human or animal lungs can become too weak to sustain a sufficient flow of oxygen to the body and to remove adequate amounts of expired carbon dioxide. Under these circumstances, it is often necessary to aid the lungs through forms of mechanical assistance, such as mechanical ventilation.

In a common form, mechanical ventilation involves the introduction of an endotracheal tube and, in some cases, a small, open-ended catheter within that tube, into the trachea of a human or animal. The distal ends of the endotracheal tube and/or catheter are positioned to rest at or slightly above the carina of the lungs. A well-humidified oxygen/air mixture is then introduced through the endotracheal tube and/or catheter to provide oxygen to the lungs. In less severe circumstances, the oxygen/air mixture can be supplied through the endotracheal tube and/or catheter using continuous positive airway pressure (CPAP). Where CPAP is used, the patient will use his or her own lung power to exhale the expired gas. In more severe circumstances, it is necessary to use mechanically controlled ventilation with a positive end expiratory pressure (PEEP).

One of the drawbacks of inserting an endotracheal tube and/or catheter into the trachea of a patient is that it reduces the lumen of the tracheal passageway and thus, without mechanical assistance, would make it more difficult for the patient to breathe. This situation is exacerbated if the endotracheal tube has a thick wall. To the extent the endotracheal tube and/or catheter is removing space from the tracheal passageway, it increases airway resistance. This airway resistance can be reduced by increasing the internal diameter of the endotracheal tube, but at a cost of increasing dead space where expired carbon dioxide gas can accumulate and be inhaled during the next breath.

There have been a number of attempts in the art to alleviate these airway resistance and dead space problems. In the inventor's earlier U.S. Pat. No. 5,429,127, which is incorporated herein by reference, a two stage ultra-thin walled endotracheal tube is disclosed which fits snugly against the contours of the trachea and uses a thin reinforcing wire to allow the endotracheal tube to be formed as thinly as possible. The ultra-thin walled endotracheal tube is effective in lowering the airway resistance as compared with thicker conventional endotracheal tubes. Also, in the inventor's earlier U.S. Pat. No. 5,687,714, a method is disclosed for preventing the distal end of an endotracheal tube catheter from becoming clogged with mucus and thereby unable to deliver fresh air to the lungs. By assuring that fresh air is delivered to the lungs, this invention reduces endotracheal tube dead space. While these inventions certainly represent important steps in the development of the tracheal ventilation art, more can still be done to address the airway resistance and dead space problems.

BRIEF SUMMARY OF THE INVENTION

The present invention provides a tracheal tube ventilation apparatus to more effectively remove expired gases and thereby lower dead space. In one preferred embodiment, this is accomplished by creating one or more leak holes in the wall of the endotracheal tube above the larynx, such as in the back of the mouth (i.e., oropharynx), so that expired gases can leak out of the endotracheal tube. Each leak hole might advantageously have a diameter between 0.5 and 4.0 mm. In another preferred embodiment, a tube is attached to a proportionately larger diameter leak hole (e.g., up to 8.0 mm) so that the expired gases can be directed away from the leak hole to a specific location, such as directed out of the mouth. In the case of mechanically controlled ventilation, a positive end expiratory pressure can be applied to this tube. In each of these embodiments, it is preferred, but not required, that the endotracheal tube be an ultra-thin walled, two stage tube so to assist in the reduction of airway resistance.

DETAILED DESCRIPTION OF THE INVENTION

Figure 1:
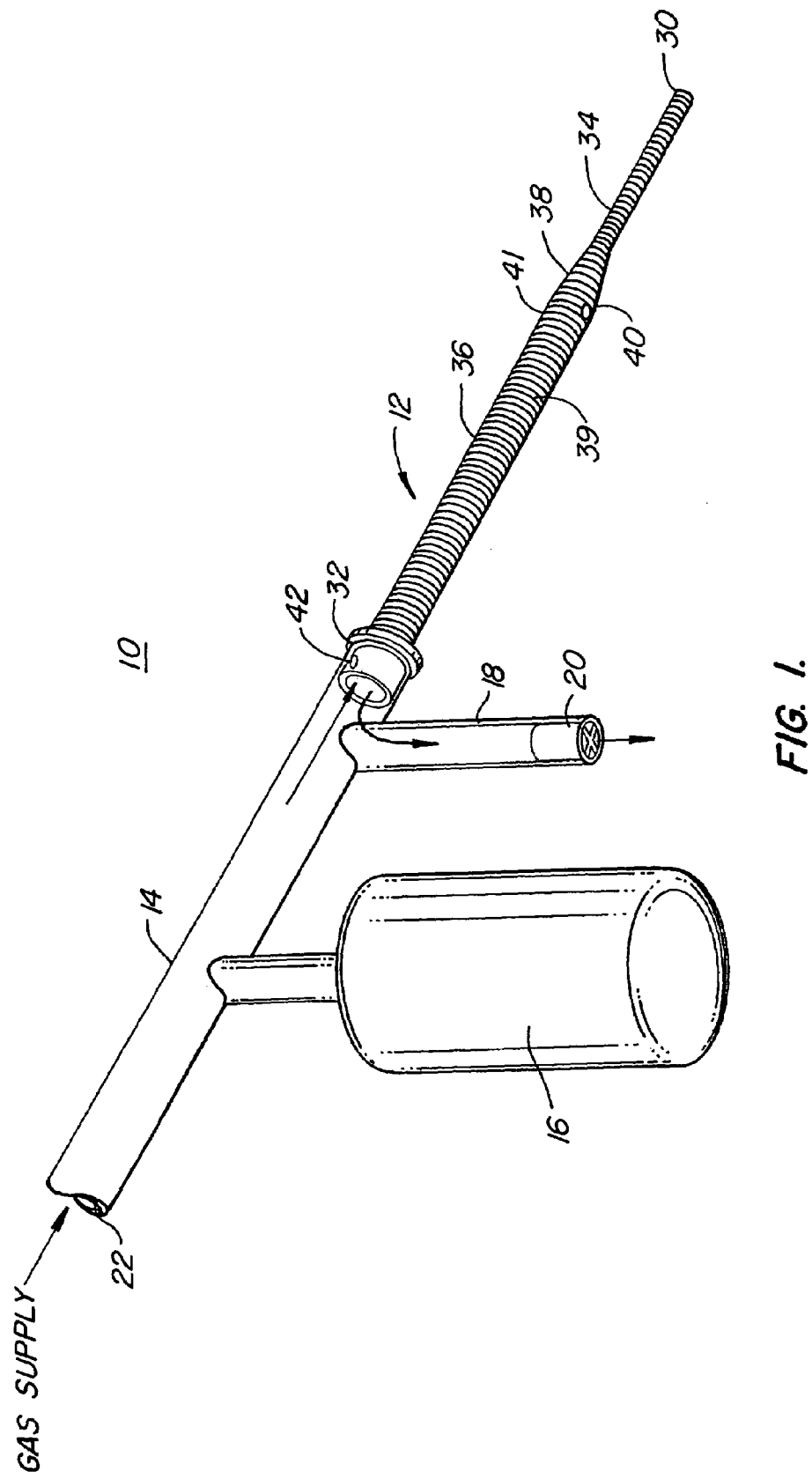
FIG. 1 shows a perspective view of a preferred CPAP embodiment of the tracheal ventilation apparatus of the present invention illustrating use of a leak hole.

FIG. 1 shows a tracheal tube ventilation apparatus 10 for CPAP ventilation which is constructed in accordance with the present invention. This tracheal tube ventilation apparatus 10 includes an endotracheal tube 12, a flexible exterior tube 14, a balloon reservoir 16 and a safety tube 18 with threshold valve 20. Through use of a gas supply to the proximal end 22 of the flexible exterior tube 14 and a continuously leaking balloon reservoir 16, the tracheal tube ventilation apparatus 10 of this embodiment is able to maintain a continuous positive airway pressure of a humidified oxygen/air mixture to the lungs of the ventilated patient. The safety tube 18 and threshold valve 20 are used as a safety device to protect the patient's lungs from being overinflated. If the pressure being supplied to the lungs becomes too great, the threshold valve 20 will open in order to release excess pressure.

The endotracheal tube 12 has an open distal end 30 and an open proximal end 32. The open distal end 30 is the end inserted into the patient's trachea, preferably to a point at or slightly above the carina of the patient's lungs. The open proximal end 32 of the endotracheal tube 12 is connected to the flexible exterior tube 14 where it receives the humidified oxygen/air mixture.

As described in the incorporated by reference U.S. Pat. No. 5,429,127, the endotracheal tube 12 of the present invention is preferably formed in two stages 34, 36 to more snugly fit against the contours of the patient's trachea and pharynx. The first or distal stage 34 has a smaller diameter in order to comfortably fit within the confined area of the lower trachea. The second or proximal stage 36 has a larger diameter, which corresponds with the larger diameter of the patient's pharynx. Connecting the two stages 34, 36 is a tapered section 38 which gradually increases in diameter from the diameter of the first stage 34 to the diameter of the second stage 36. By having a larger diameter second stage, this preferred form of endotracheal tube 12 is able to greatly reduce the resistance to airflow in the second stage portion as compared with common, single diameter endotracheal tubes.

Figure 2:
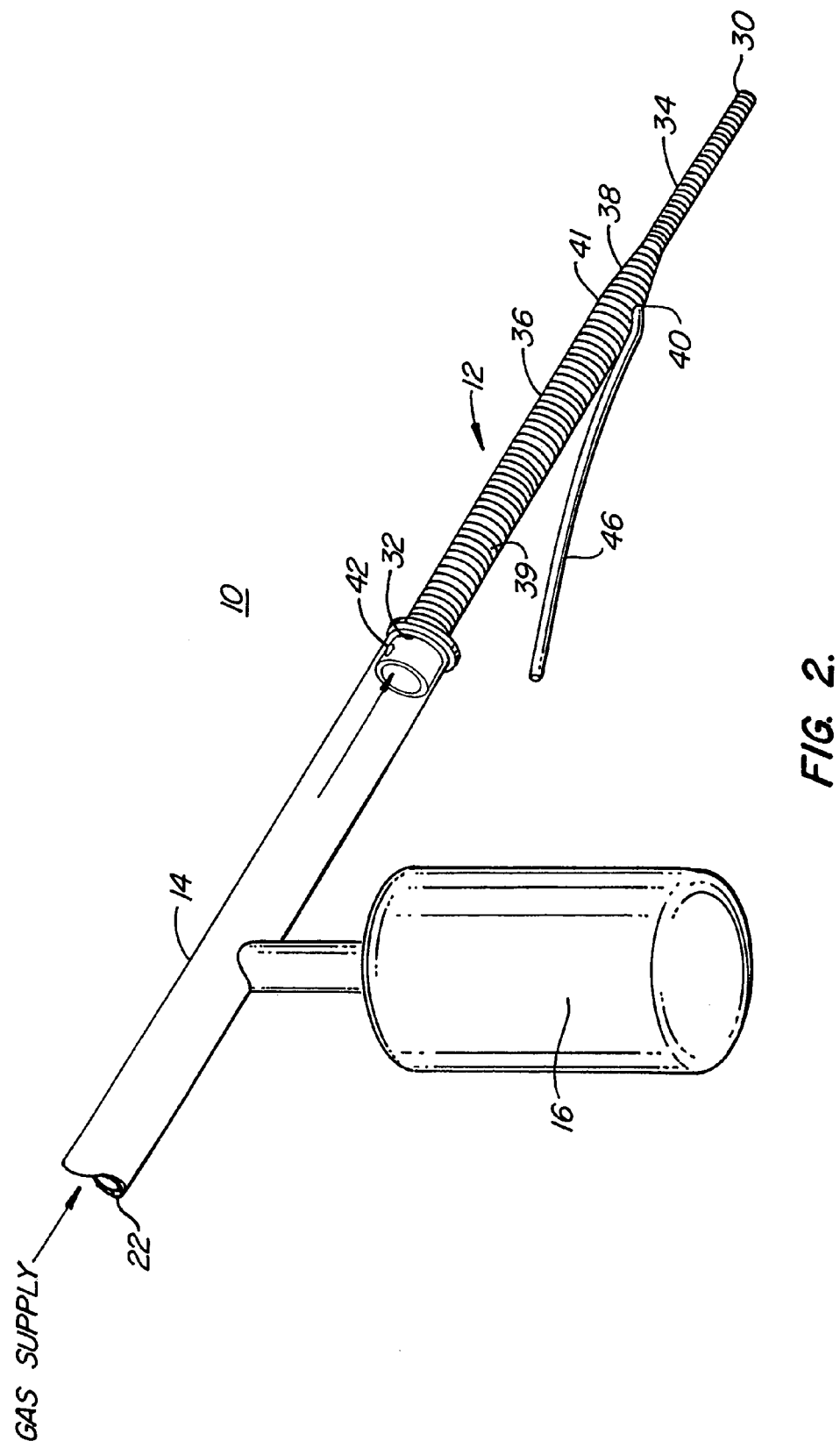
FIG. 2 shows a perspective view of a second preferred CPAP tracheal ventilation apparatus embodiment of the present invention illustrating the use of a tube extending from the leak hole.

As also described in U.S. Pat. No. 5,429,127, the endotracheal tube of the present invention preferably has an ultra-thin wall construction. This ultra-thin wall construction can be achieved by reinforcing a plastic endotracheal tube with a very strong wire 39. While it is most helpful to at least form the small diameter distal stage 34 of the endotracheal tube using a wire reinforced, ultra-thin wall construction, it is nonetheless preferred that both stages 34, 36 be formed using the wire reinforced, ultra-thin wall construction as shown in FIGS. 1 and 2. A preferred choice of wire for this application is a superelastic nickel titanium alloy memory wire referred to as "Nitinol." This Nitinol memory wire can be purchased from such vendors as Fort Wayne Metal of Fort Wayne, Ind. This Nitinol memory wire exhibits remarkable kink resistance, thereby rendering the wire reinforced endotracheal tube 12 virtually crush proof. This is a particularly important feature when dealing with endotracheal tubes of a wall thickness of about 0.2 mm or less. While a standard form of endotracheal tube wall thickness, without wire reinforcement, may be over 0.8 mm thick, an ultra-thin walled endotracheal tube with Nitinol wire reinforcement has been successfully formed and used with a wall thickness of only 0.15 mm.

The preferred two stage endotracheal tube 12 of the present invention can be constructed in several ways. For example, the Nitinol wire 39 can be wrapped around a two diameter Teflon® coated mandrel. A plastic solution, such as a polyurethane plastic solution, can be formed around the wire wrapped mandrel to a suitable thickness and allowed to harden. After the plastic has sufficiently hardened, the wire reinforced endotracheal tube can be removed from the mandrel for use. Alternatively, the wire and endotracheal tube can be extruded simultaneously using a suitable form of extrusion machine.

While the two stage and ultra-thin wall construction techniques are preferred for manufacturing the endotracheal tubes 12 for the present invention, the leak hole and leak hole tube aspects of the present invention are also applicable to more standard, single diameter types of endotracheal tubes. Such a leak hole 40 is illustrated in FIG. 1. The basic purpose of the leak hole 40 is to allow expiratory gases to be removed from the endotracheal tube as soon as practicable in order to lower dead space. An advantageous position for such a leak hole is in that portion of the endotracheal tube wall 41 which is located above the larynx, such as in the back of the mouth (i.e., oropharynx). If the leak hole is positioned in the larynx or below, it will likely be blocked or otherwise unable to achieve its purpose of removing expiratory gases.

As shown in FIG. 1, on a two stage endotracheal tube 12, an oropharynx leak hole position 40 would typically correspond to the distal end of the second stage 36. While a range of different diameters can be used for the leak hole 40, the inventor has found, for example, that a diameter of between 0.5 and 4.0 mm can be effective in achieving the leak hole's purpose. Moreover, the leak hole 40 of the present invention need not be limited to being a single leak hole, nor need it be limited to being in the endotracheal tube 12 itself. As shown in FIG. 1, for example, a second leak hole 42 can be formed at the distal end of the flexible exterior tube 14. This second leak hole 42 can be particularly useful in the rare event that the patient's expiratory flow pressure exceeds the pressure of the balloon reservoir 16.

Turning now to FIG. 2, a second CPAP tracheal tube ventilation apparatus 10 embodiment is illustrated. As in FIG. 1, this CPAP tracheal tube ventilation apparatus 10 also includes a two stage endotracheal tube 12, a flexible exterior tube 14 and a balloon reservoir 16. In the context of the present invention, the primary difference between the FIG. 1 and FIG. 2 embodiments is that, in FIG. 2, a flexible tube 46 is connected to a proportionately larger leak hole 40 to direct gases away from the leak hole. This proportionately larger leak hole 40 might advantageously be made, for example, up to 8.0 mm in diameter. While this tube 46 does add resistance to the flow of expired gases from the leak hole, it nonetheless has the advantage of allowing gases to be directed to a particular location, such as out of the patient's body altogether. In this way, expired gases will be better prevented from collecting at or above of the leak hole.

Figure 3:
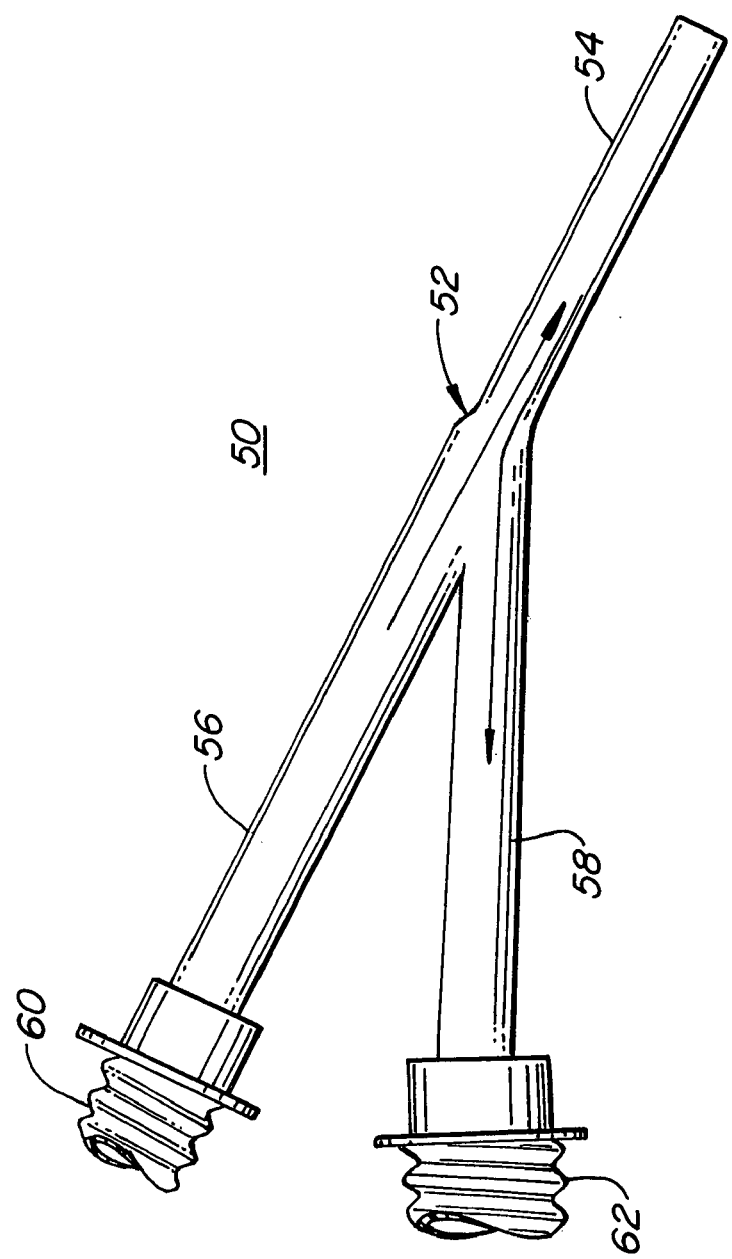
FIG. 3 shows a perspective view of a third preferred embodiment of the present invention which can be used for either CPAP or mechanically controlled ventilation.

A variation of the leak hole tube concept of FIG. 2 for either mechanically controlled or CPAP ventilation is shown in FIG. 3. In FIG. 3 the tracheal ventilation apparatus 50 again has an endotracheal tube 52 with two stages. These can be with or without (as shown) the wire reinforced, ultra-thin walled construction illustrated in FIGS. 1 and 2. As before, there is a distal or first stage tube 54, which is inserted into the patient's trachea. In this case, though, there are two proximal or second stage tubes 56, 58, instead of one. Both of these proximal or second stage tubes 56, 58 are connected to their respective external tubing 60, 62. One of the proximal stage tubes 56 is used for supplying a humidified oxygen/air mixture to the patient. The other proximal stage tubes 58 is used for removing expired gases out of the patient's lungs. The operation of the supplying fresh air to and withdrawing expired gas from the patient's lungs can be timed to correspond to a normal breathing pattern. Those of skill in the art will recognize that there is no special order to the inspiratory 56 and expiratory 58 proximal stage tubes. The inspiratory proximal stage tube 56 could just as easily be used for expiration and vice versa.

Although the invention has been described in reference to specific exemplary embodiments, it will be appreciated by those in the art that the invention is intended to cover all modifications and equivalents to those embodiments. For example, those of skill in the art will immediately recognize that the leak holes and endotracheal tube cross-sections can be formed in shapes which are not circular (e.g., oval, hexagonal etc.). For these reasons, the scope of Applicant's invention is only limited by the appended claims.

What is claimed is:

1. A tracheal tube ventilation apparatus for ventilation of human or animal lungs comprising:

an endotracheal tube for insertion into a human or animal trachea having open proximal and distal ends, solid side walls and one or more leak holes formed through said solid endotracheal tube side walls, wherein said endotracheal tube has a smaller cross-sectional stage for insertion within the trachea and a larger cross-sectional stage for insertion above the trachea and wherein, when inserted, said one or more leak holes are at a position within said human or animal above the larynx; and, a source to provide humidified air flow entering through the proximal end of said endotracheal tube and exiting into said human or animal lungs primarily through the distal end of said endotracheal tube.

2. The tracheal tube ventilation apparatus of claim 1 wherein at least one of said leak holes is positioned approximately in the area joining said smaller cross-sectional stage and said larger cross-sectional stage.

3. A tracheal tube ventilation apparatus for ventilation of human or animal lungs comprising:
   an endotracheal tube for insertion into a human or animal trachea having open proximal and distal ends, solid side walls and one or more leak holes formed through said solid endotracheal tube side walls, wherein, when inserted, said one or more leak holes are at a position within said human or animal above the larynx and wherein a further tube is attached to at least one of said endotracheal tube leak holes; and,
   a source to provide humidified air flow entering through the proximal end of said endotracheal tube and exiting into said human or animal lungs primarily through the distal end of said endotracheal tube.

4. The tracheal tube ventilation apparatus of claim 3 wherein exhaust gases are removed through said further tube.

5. A tracheal tube apparatus for the ventilation of human or animal lungs comprising:
   an endotracheal tube for insertion into a human or animal trachea having open proximal and distal ends, solid side walls and one or more leak holes formed through said solid endotracheal tube side walls, wherein said endotracheal tube has a smaller cross-sectional stage for insertion within the trachea, a larger cross-sectional stage for insertion above the trachea and at least one leak hole positioned in said larger cross-sectional stage to facilitate removal of expired gases from said endotracheal tube; and
   a source to provide humidified air flow entering through the proximal end of said endotracheal tube and exiting into said human or animal lungs primarily through the open distal end of said endotracheal tube.

6. The tracheal tube ventilation apparatus of claim 5 further comprising a flexible exterior tube and a balloon reservoir connected to said endotracheal tube.

7. The tracheal tube ventilation apparatus of claim 5 wherein the walls of at least a portion of said endotracheal tube are formed from a thin, wire reinforced plastic.

8. The tracheal tube ventilation apparatus of claim 7 wherein said endotracheal tube plastic is polyurethane.

9. The tracheal tube ventilation apparatus of claim 7 wherein said reinforcing wire is made of superelastic nickel titanium alloy.

10. The tracheal tube ventilation apparatus of claim 5 wherein each of said holes is circular and between 0.5 and 4.0 mm in diameter.

* * * * *